United States Patent
Wu

(10) Patent No.: US 9,826,908 B2
(45) Date of Patent: Nov. 28, 2017

(54) DEVICES, SYSTEMS AND METHODS FOR TESTING CARDIAC EXERCISE FUNCTIONS

(71) Applicant: SmartHealth Electronics Ltd., Jiangsu Province (CN)

(72) Inventor: Jiankang Wu, Beijing (CN)

(73) Assignee: SmartHealth Electronics Ltd., Jiangsu Province (CN)

( * ) Notice: Subject to any disclaimer, the term of this patent is extended or adjusted under 35 U.S.C. 154(b) by 0 days.

(21) Appl. No.: 15/140,924

(22) Filed: Apr. 28, 2016

(65) Prior Publication Data

US 2016/0317044 A1    Nov. 3, 2016

(30) Foreign Application Priority Data

Apr. 30, 2015  (CN) .......................... 2015 1 0217071
Apr. 22, 2016  (CN) .......................... 2016 1 0256974

(51) Int. Cl.
*A61B 5/04* (2006.01)
*A61B 5/0205* (2006.01)
(Continued)

(52) U.S. Cl.
CPC .......... *A61B 5/0205* (2013.01); *A61B 5/0006* (2013.01); *A61B 5/0245* (2013.01);
(Continued)

(58) Field of Classification Search
CPC ... A61B 5/0205; A61B 5/0006; A61B 5/0245; A61B 5/0404; A61B 5/1118;
(Continued)

(56) References Cited

U.S. PATENT DOCUMENTS

2007/0016098 A1* 1/2007 Kim .................. A61B 5/02055
                                                  600/546
2013/0171599 A1* 7/2013 Bleich ................. A61B 5/0456
                                                  434/247

(Continued)

OTHER PUBLICATIONS

Meng, Xiaoli, et al., "Hierarchical Information Fusion for Global Displacement Estimation in Microsensor Motion Capture", IEEE Transactions on Biomedical Engineering, vol. 60, No. 7,, (Jul. 2013), 2053-2063.

(Continued)

*Primary Examiner* — Robert N Wieland
(74) *Attorney, Agent, or Firm* — Schwegman Lundberg & Woessner, P.A.

(57) ABSTRACT

The present disclosure discloses a device, system and method for testing cardiac exercise functions. Chronotropic Competence Indices (CCIs) are proposed to quantitatively describe the adaptation capability of cardiopulmonary system in response to exercise intensity variation in terms of heart rate changes, and thereby describes the dynamic process of the heart in the body metabolic process. The present disclosure discloses a device which measures the CCIs in real time by using the wearable technology, and referred to as Cardiac Exercise Test (CET). Compared with the Cardiopulmonary Exercise Testing (CPX) and parameters measured by the CPX such as a maximum oxygen uptake, the CCIs have clear clinical meanings and specific normal reference values; and the CET reduces the risk of the test. It is simple to use, and can be used anytime anywhere. It is of great importance in wide clinical applications, and is of great significance in prevention and rehabilitation of cardiopulmonary disease.

19 Claims, 4 Drawing Sheets

(51) Int. Cl.
| | |
|---|---|
| *A61B 5/00* | (2006.01) |
| *A61B 5/0245* | (2006.01) |
| *A61B 5/0404* | (2006.01) |
| *A61B 5/044* | (2006.01) |
| *A61B 5/11* | (2006.01) |
| *A61B 5/22* | (2006.01) |
| *G06F 19/00* | (2011.01) |

(52) U.S. Cl.
CPC ............ *A61B 5/044* (2013.01); *A61B 5/0404* (2013.01); *A61B 5/1118* (2013.01); *A61B 5/222* (2013.01); *A61B 5/4884* (2013.01); *A61B 5/6802* (2013.01); *A61B 5/6823* (2013.01); *A61B 5/6828* (2013.01); *A61B 5/6895* (2013.01); *A61B 5/742* (2013.01); *A61B 5/7405* (2013.01); *A61B 5/746* (2013.01); *A61B 5/747* (2013.01); *G06F 19/3406* (2013.01); *G06F 19/3437* (2013.01); *G06F 19/3481* (2013.01)

(58) Field of Classification Search
CPC ..... A61B 5/222; A61B 5/4884; A61B 5/6802; A61B 5/6823; A61B 5/6828; G06F 19/3406; G06F 19/3481
See application file for complete search history.

(56) References Cited

OTHER PUBLICATIONS

Zheng, Huabin, et al., "A Real-Time QRS Detector Based on Discrete Wavelet Transform and Cubic Spline Interpolation", Telemedicine and e-Health vol. 14 No. 8, (2008), 809-815.

* cited by examiner

DEVICES, SYSTEMS AND METHODS FOR TESTING CARDIAC EXERCISE FUNCTIONS

CROSS-REFERENCE TO RELATED APPLICATION(S)

This application claims priority to the Chinese Patent Application No. 201510217071.1, filed on Apr. 30, 2015, entitled "DEVICES, SYSTEMS AND METHODS FOR TESTING CARDIAC EXERCISE FUNCTIONS" and the Chinese Patent Application No. 201610256974.5, filed on Apr. 22, 2016, entitled "DEVICES, SYSTEMS AND METHODS FOR TESTING CARDIAC EXERCISE FUNCTIONS" which are incorporated herein by reference in their entireties.

TECHNICAL FIELD

The present disclosure relates to the field of medical detection technology, and more particularly, to a wearable device, system and method for digital cardiopulmonary function exercise testing.

BACKGROUND

Cardiovascular disease is the first killer for people. 20% of people in Europe and America have cardiovascular disease, and 290 million people in China have cardiovascular disease. Prevention, diagnosis and rehabilitation of cardiovascular disease are heavily dependent on assessment of cardiovascular system function. A function of a cardiopulmonary circulatory system is to ensure normal operations of various activities of a human body. An exercise can only be completed with a closely coordinated operation among visceral organs in the cardiopulmonary circulatory system. Cardiopulmonary Exercise Testing (CPX) is a scientific tool for assessing cardiopulmonary functions during an exercise. The CPX is to assess reaction of visceral organs such as heart, lung or the like to the exercise by monitoring oxygen uptake (VO2), carbon dioxide output (VCO2), Heart Rate (HR), voluntary ventilation (VE) or the like of an organism in an exercise state. The CPX has noninvasive and quantitative features, which are of great value for diagnosis and prognosis of cardiopulmonary disease. On the other hand, a physiological mechanism of the cardiopulmonary circulatory system and the principle of the CPX measurement method are relatively complex, which are not easily understood by clinical doctors and nurses. Quite a few medical staff, no matter whether in the cardiovascular section or in the pulmonary section, has insufficient knowledge on both the CPX usage and interpretation of its measurements thereof.

Further, although measurement parameters of the CPX are quantitative, testees are required to achieve an exercise limit. As patients often cannot achieve the exercise limit or an operator cannot accurately determine the exercise limit, the measurement results may loss their effects as supposed.

An ECGgram (ECG) exercise test, which is also called ECG exercise load test, is a method for observing ECG changes by increasing a cardiac load through a certain amount of exercise, so as to implement clinical assessment on the known or suspected cardiovascular disease, especially coronary atherosclerotic cardiac disease (CHD). Analysis content for such method comprises exercise capabilities, clinical symptoms, haemodynamics and ECG changes. The content is analyzed and determined qualitatively by doctors, and does not provide quantitative indices.

"6 minutes walking test" is a simple method for testing cardiopulmonary dynamic functions. In 2002 and 2005, the 6 minutes walking test is explicitly designated as an index for assessing a cardiac function in the Guide for diagnosis and treatment of chronic heart failure issued by ACC/AHA. Currently, a universal method is to draw a 100 feet straight line on a flat ground with a chair arranged respectively on two ends thereof, and then measure a walking distance of a trainee after the trainee walks along the straight line as quickly as possible and stops until 6 minutes. The longer the walking distance is, the larger the indicated exercise tolerance is, and the better the cardiac function is. Although the 6 minutes walking test is simple, it is a full manual operation, needs a place, has simplex measurement parameters, and largely depends on personal willingness.

Due to the above different disadvantages in the related art, there is an urgent need for a new generation of assessment technology for cardiac rehabilitation.

SUMMARY

In order to solve the problem in the related art that the device is complex and the testee must achieve a limit exercise state in the CPX, the present disclosure aims to measure an exercise signal and an ECG signal of the testee in a walking state on a flat ground or in an exercise state on a treadmill in real time, so as to calculate exercise parameters, ECG parameters and Chronotropic Competence Indices (CCIs) of the testee.

In an aspect of the present disclosure, a system for testing cardiac exercise functions is provided, comprising:

at least one wearable component worn by a testee, comprising an ECG acquisition module configured to acquire an ECG signal of the testee, and an exercise acquisition module configured to acquire an exercise signal of the testee without or with a load;

a handhold electronic device configured to acquire the ECG signal and the exercise signal of the testee from the at least one wearable component in a wired or wireless communication manner, process the ECG signal and the exercise signal, and control a process of cardiac exercise testing; and a workstation connected to the handhold electronic device in a wireless or wired communication manner, configured to receive data from the handhold electronic device, complete the process of cardiac exercise testing under the monitoring of a user, and generate a test report comprising at least ECG parameters, exercise parameters and Chronotropic Competence Indices (CCIs).

Preferably, the handhold electronic device is configured to process the ECG signal and the exercise signal in real time in the following three periods of resting for at least 1 minute before an exercise test, exercising for 6 minutes or more in a certain mode after the exercise test is started, and resting for 1 minute or more after the exercise is stopped.

Preferably, the CCIs comprise Resting Heart Rate (RHR), Chronotropic Limit (CL), Chronotropic Rate (CR), and Heartrate Recovery after Exercise (HRE).

Preferably, the CR is measured according to the following equation:

$$CR=(HR_{stage}-HR_{rest})/(MET_{stage}-1)$$

wherein $HR_{stage}$ and $MET_{stage}$ represent a heart rate and an exercise metabolic equivalent of the testee at a certain time during the test respectively, and $HR_{rest}$ represents a heart rate of the testee during resting.

Preferably, the chronotropic limits measured according to the following equation:

$$CL=(HR_{max}-HR_{rest})/(HR_{PredM}-HR_{rest})$$

wherein $HR_{max}$ and $HR_{rest}$ represent a maximum heart rate and a Resting Heart Rate (RHR) respectively, and $HR_{PredM}$ represents a predicted value of the maximum heart rate.

Preferably, the HRE is defined as a difference between a maximum exercise heart rate and a heart rate 1 minute after the exercise is stopped, which represents a speed at which the heart rate recovers to the RHR after the exercise is stopped.

Preferably, the handhold electronic device comprises a man-machine interaction module configured to alert the testee of start or stop of the exercise or acceleration or deceleration of the exercise in a voice or image manner, and display information, an exercise mode, and an ECG signal of the testee in real time, and configured with an emergency button for use by the testee when feeling uncomfortable.

Preferably, the ECG acquisition module is worn on the chest of the testee, and comprises at least one lead, and the exercise acquisition module is configured to measure exercise acceleration and an attitude angle of the testee during the exercise.

Preferably, the exercise acquisition module comprises an exercise sensing unit arranged on a torso of the testee and exercise sensing units arranged on two legs of the testee.

In another aspect of the present disclosure, a system for testing cardiac exercise functions is provided, comprising:

at least one wearable component worn by a testee, comprising an ECG acquisition module configured to acquire an ECG signal of the testee;

a treadmill comprising an exercise acquisition module configured to acquire an exercise signal of the testee without or with a load, and an electronic device configured to acquire the ECG signal of the testee from the at least one wearable component and the exercise signal of the testee from the exercise acquisition module in a wired or wireless communication manner, process the ECG signal and the exercise signal, and control a process of cardiac exercise testing; and a workstation connected to the electronic device in a wireless or wired communication manner, configured to receive data from the electronic device, complete the process of cardiac exercise testing under the monitoring of a user, and generate a test report comprising at least ECG parameters, exercise parameters and Chronotropic Competence Indices (CCIs).

Preferably, the exercise acquisition module comprises a speed sensor and a gradient sensor arranged on the treadmill.

Preferably, the CCIs comprise a Resting Heart Rate (RHR), a Chronotropic Limit (CL), a Chronotropic Rate (CR), and a Heartrate Recovery after Exercise (HRE).

In a further aspect of the present disclosure, a device for testing cardiac exercise functions is provided, comprising:

an exercise acquisition module configured to acquire an exercise signal of a testee without or with a load, wherein at least one wearable component is worn by the testee, and comprises an ECG acquisition module configured to acquire an ECG signal of the testee; and an electronic device configured to acquire the ECG signal of the testee from the at least one wearable component and the exercise signal of the testee from the exercise acquisition module in a wired or wireless communication manner, process the ECG signal and the exercise signal, and control a process of cardiac exercise testing, wherein the process of cardiac exercise testing is completed according to the data of the electronic device under the monitoring of a user, and a test report is generated, wherein the test report comprises at least ECG parameters, exercise parameters and Chronotropic Competence Indices (CCIs).

In a further aspect of the present disclosure, an electronic device is provided, comprising:

a communication module configured to acquire an ECG signal of a testee and an exercise signal of the testee without or with a load from at least one wearable component worn by the testee in a wired or wireless communication manner;

a signal processing module configured to process the ECG signal and the exercise signal obtained by the communication module in the following three periods of resting for at least 1 minute before an exercise test, exercising for 6 minutes or more in a certain mode after the exercise test is started, and resting for 1 minute or more after the exercise is stopped; and a control module configured to control a process of cardiac exercise testing.

In a further aspect of the present disclosure, a method for testing cardiac exercise functions is provided, comprising:

perceiving, by at least one wearable component worn by a testee, an ECG signal of the testee and an exercise signal of the testee without or with a load;

processing the ECG signal and the exercise signal, and controlling a process of cardiac exercise testing, wherein the process of cardiac exercise testing comprises the following three periods of resting for at least 1 minute before an exercise test, exercising for 6 minutes or more in a certain mode after the exercise test is started, and resting for 1 minute or more after the exercise is stopped; and completing the process of cardiac exercise testing under the monitoring of a user, and generating a test report comprising at least ECG parameters, exercise parameters and Chronotropic Competence Indices (CCIs).

The solution of the above embodiments can reflect the cardiovascular dynamic functions, which is easier to apply than the CPX.

BRIEF DESCRIPTION OF THE DRAWINGS

For better understanding the present disclosure, the present disclosure will be described in detail below in conjunction with accompanying drawings.

DETAILED DESCRIPTION

Figure 1:
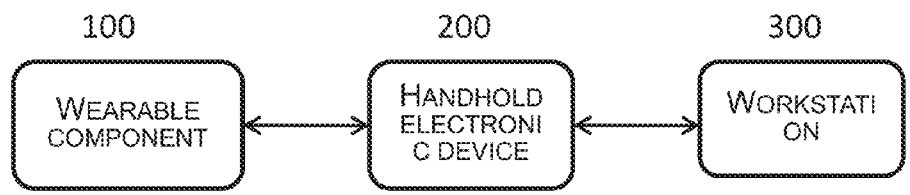
FIG. 1 is a structural diagram illustrating a device and system for testing cardiac exercise functions according to an embodiment of the present disclosure.

The specific embodiments of the present disclosure will be described in detail below. It should be noted that the embodiments herein are used for illustration only, without limiting the present disclosure. In the description below, a number of specific details are explained to provide better understanding of the present disclosure. However, it is apparent to those skilled in the art that the present disclosure can be implemented without these specific details. In other instances, well known circuits, materials or methods are not described specifically so as not to obscure the present disclosure.

Throughout the specification, the reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" occurred in various positions throughout the specification may not necessarily refer to the same embodiment or example. Furthermore, specific features, structures or properties may be combined into one or more embodiments or examples in any appropriate combination and/or sub-combination. Moreover, it should be understood by those skilled in the art that the term "and/or" used herein means any and all combinations of one or more listed items.

According to some embodiments of the present disclosure, a device and system for digital cardiac exercise testing comprise a wearable component, a handhold electronic device, and a workstation. The wearable component detects an ECG signal and an exercise signal of a testee during resting and during an exercise, and transmits the signals to the handhold electronic device. The handhold electronic device receives the ECG signal and the exercise signal from the wearable component, processes and analyzes these signals, detects a QRS structure of the ECG signal and an ECG abnormality, and analyzes an exercise speed and intensity. The handhold electronic device controls and alerts a process of the whole exercise test, warns a possible abnormality, and alerts exercise precautions in a voice manner. The handhold electronic device further transmits the signals and an analysis result to the workstation. The workstation displays the signals and the analysis result in real time, further analyzes and processes the ECG signal and the exercise signal, calculates parameters such as Chronotropic Competence indices, and generates a test report.

For example, the device and system for cardiac exercise testing may be implemented in two device forms. One device form is a walking exercise form on a horizontal ground, which is called "Digital Cardiac Walking Test". A wearable component is worn on the chest, to collect a single-lead or multi-lead ECG and a human body exercise signal, and transmit the collected signals to the handhold electronic device in a Bluetooth or another wireless communication manner. The handhold electronic device is a computing device similar to an intelligent mobile phone or a tablet computer, which receives and processes the ECG signal and the exercise signal, and interacts with a testee in a voice manner on an interactive screen; controls the process of exercise testing, alerts an exercise manner and a speed, and warns an ECG abnormality; calculates and displays an ECG, an HR, a stride frequency, a step length, a distance and exercise intensity represented by a metabolic equivalent; and transmits the signals and the calculation results to the workstation in a wireless manner.

The other device manner is an exercise manner by virtue of a treadmill, which is called "Digital Cardiac Treadmill Test". A wearable component collects a single-lead or multi-lead ECG, and transmits the collected signal to the handhold electronic device in a wired or wireless manner. The handhold electronic device may be for example a treadmill console. The handhold electronic device also interacts with a testee in a voice manner on an interactive screen; controls the process of exercise testing, alerts an exercise manner and a speed, and warns an ECG abnormality; calculates and displays an ECG, an HR, a stride frequency, a distance and exercise intensity represented by a metabolic equivalent; and transmits the signals and the calculation results to the workstation in a wired or wireless manner. Compared with the walking exercise manner on a horizontal ground, the exercise form on a treadmill not only comprises walking on a horizontal ground, but also comprises walking and running on a slope. Information on the speed and the exercise intensity is primarily from the treadmill console.

The device for digital cardiac walking exercise test can be used anytime anywhere, and the device for Digital Cardiac Treadmill Test can be managed centrally, that is, they have respective advantages. As these devices have common advantages of intelligence, quantitative features, and convenience of use, they can provide technical and device support for popularization of cardiac function dynamic test and generalization of prevention and rehabilitation of cardiac disease.

As shown in the structural block diagram of the device and system for digital cardiac exercise testing according to the present disclosure in FIG. 1, the embodiments of the present disclosure relate to a wearable system for real-time measurement, monitoring and analysis based on a human body intelligent perceptive technology. The whole device and system for digital cardiac exercise testing is comprised of a wearable component 100, a handhold electronic device 200, and a workstation 300. The wearable component 100 is worn on the chest of a testee, to detect an ECG signal and an exercise signal of the testee. The handhold electronic device 200 is a computing component having a communication function. The handhold electronic device 200 receives the ECG signal and the exercise signal from the wearable component 100, interacts with the testee, controls the process of exercise test, and uploads test data and a processing result to the workstation 300. The workstation 300 receives the data from the handhold electronic device 200, interacts with medical workers, generates a test report, stores complete test data, an analysis result and a conclusion of the whole cardiac exercise test in a database, and uploads the test data and a report to a hospital information system. The device and system for digital cardiac exercise test according to the present disclosure collects the ECG signal and the exercise signal of the testee in an exercise scenario, and provides ECG parameters, exercise parameters and Chronotropic Competence indices of the testee.

Figure 2:
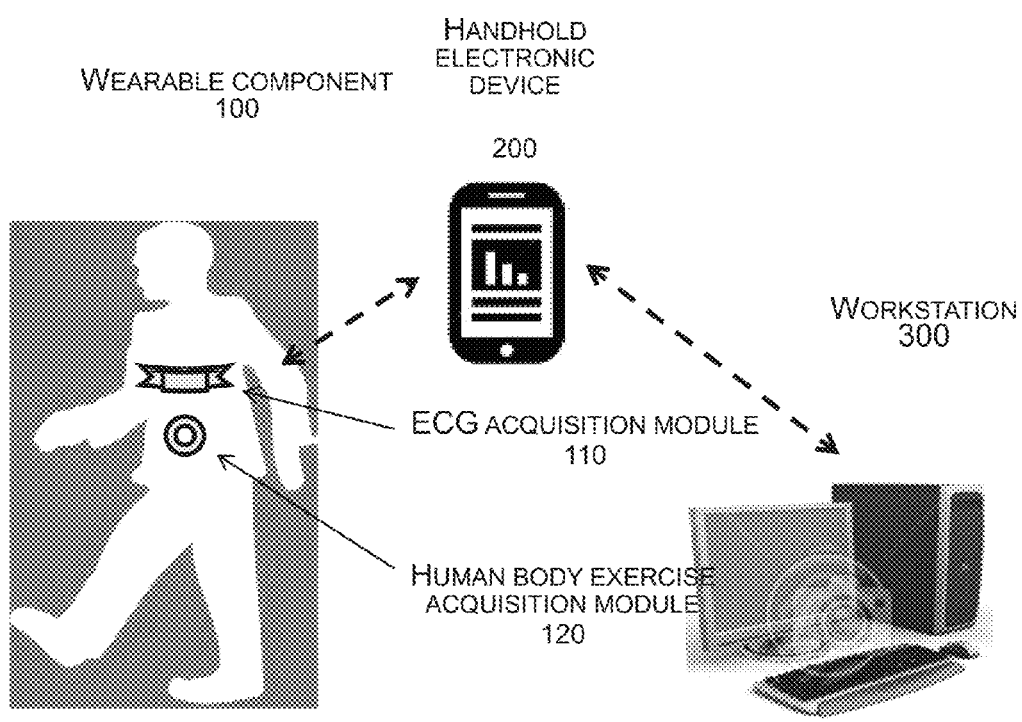
FIG. 2 is a structural diagram illustrating a device for testing cardiac exercise functions in a walking mode according to an embodiment of the present disclosure.

FIG. 2 is a diagram of an embodiment of a horizontal walking exercise form of a device for digital cardiac exercise test according to the present disclosure. The device is also called a device for "Digital Cardiac Walking Test".

An ECG acquisition module 110 is a standard ECG signal collection unit, and is comprised of 1-12 lead electrodes, an ECG signal amplifier, an analog-to-digital converter, a controller and a communication circuit. Here, in order to acquire a good quality of the ECG signal in an exercise state, electrodes which adapt to the exercise state are used. The electrodes are in close contact with a skin, and remove exercise noises with a specialized signal filtering method. A human body exercise acquisition module 120 is comprised of an exercise sensor worn on the chest, or is comprised of three exercise sensors, which are on the chest and two legs respectively. The ECG acquisition module 110 and the human body exercise acquisition module 120 upload the ECG signal and the exercise signal to the handhold electronic device 200. Here, the handhold electronic device 200 is a computing and communication unit similar to an intelligent mobile phone and a tablet computer. The handhold electronic device 200 processes the ECG signal and the exercise signal, interacts with a testee, and receives and uploads data to the workstation 300. The workstation 300 displays the received signal in real time, further analyzes, displays, and reports the ECG signal, the exercise signal and Chronotropic Competence indices, interacts with medical workers, and uploads measurement data and a report to the hospital information system.

Figure 3:
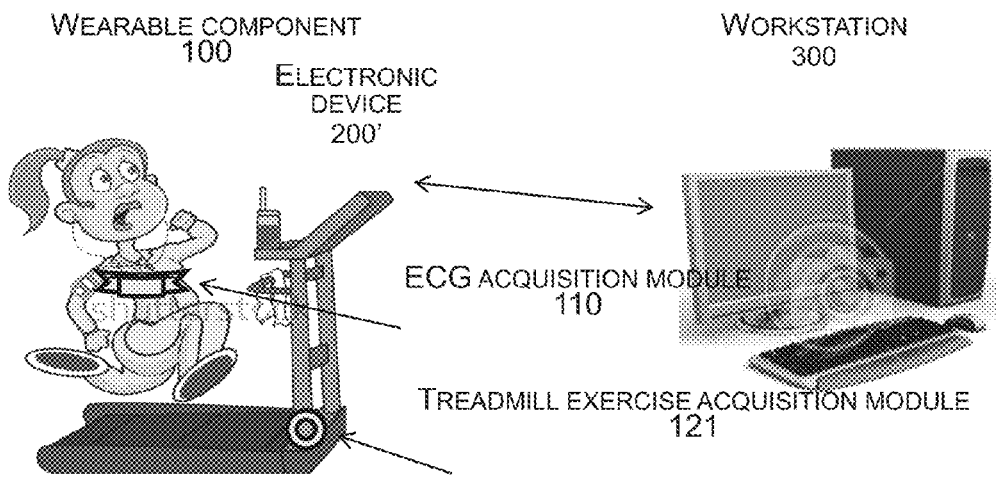
FIG. 3 is a structural diagram illustrating a device for testing cardiac exercise functions in a treadmill mode according to an embodiment of the present disclosure.
Figure 4:
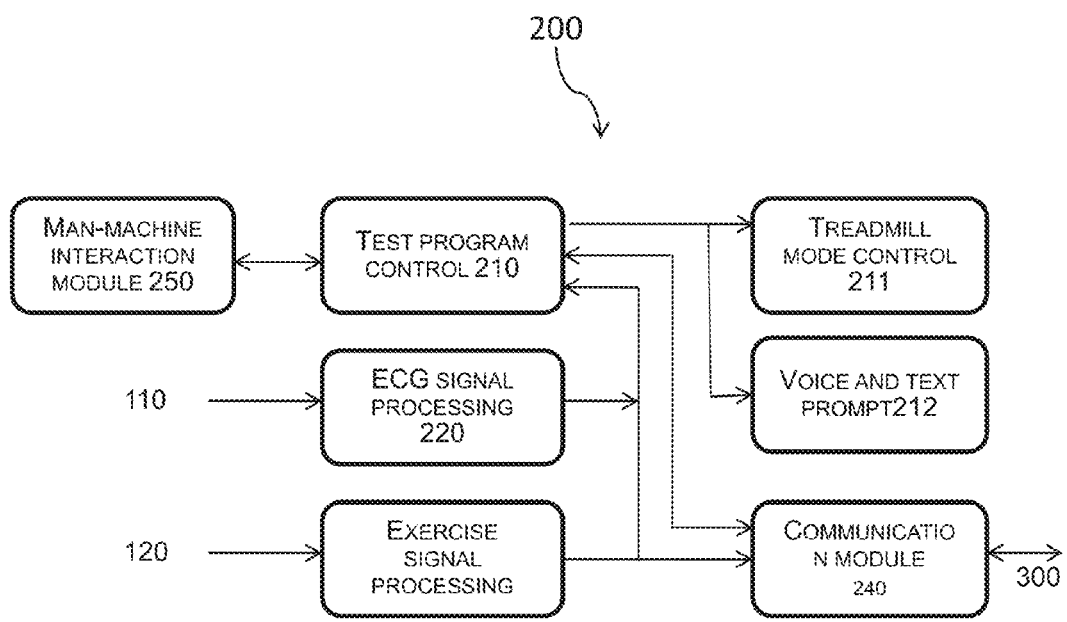
FIG. 4 is a structural diagram of a handhold electronic device in a system for testing cardiac exercise functions according to an embodiment of the present disclosure.
Figure 5:
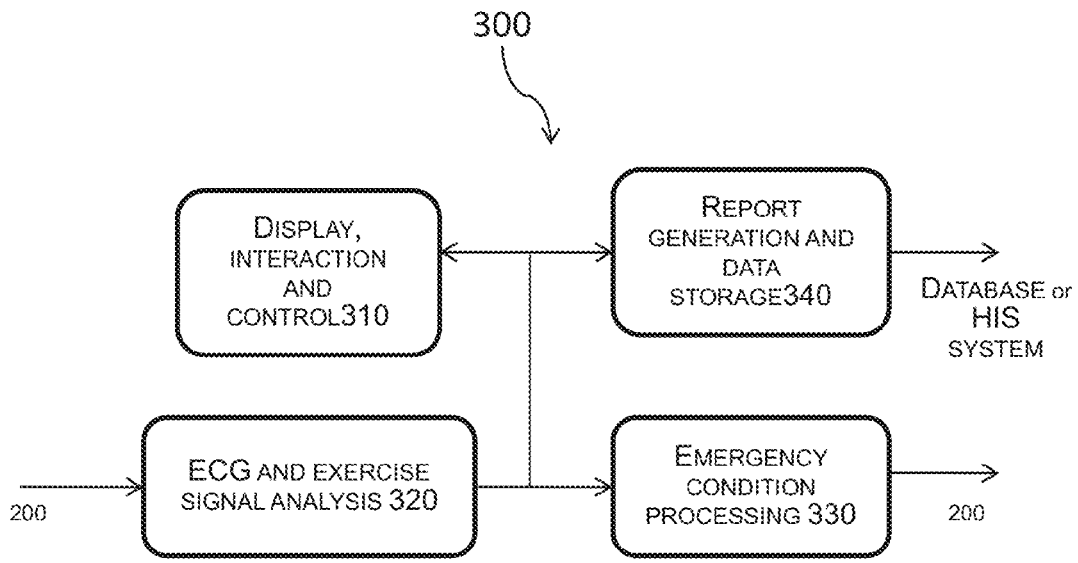
FIG. 5 is a structural diagram of a workstation in a system for testing cardiac exercise functions according to an embodiment of the present disclosure.

FIG. 3 illustrates a diagram of an embodiment of a treadmill exercise form of a device for digital cardiac exercise test according to the present disclosure. The device is also called a device for "Digital Cardiac Treadmill Test", as shown in FIG. 3.

The embodiment of FIG. 3 is basically the same as that of the "Digital Cardiac Walking Test" in FIG. 2, and the difference is as follows. Firstly, a treadmill exercise acquisition module 121 comprises a speed sensor and a gradient sensor of the treadmill, and exercise intensity represented by the metabolic equivalent is calculated according to the two parameters of speed and gradient. Secondly, the electronic device 200' here is a treadmill console, which is implemented by a tablet computer. As an exercise of a person on a treadmill is decided by an exercise mode of the treadmill, the control of the whole exercise test procedure is completed by a treadmill mode controller 211 in the electronic device 200'. Finally, the electronic device 200' is generally connected to the workstation in a wired manner.

The wearable component 100 has two types of sensors therein. One type of sensor is an ECG acquisition module 110, and the other type of sensor is a human body exercise acquisition module 120 and/or a treadmill exercise acquisition module 121.

The ECG acquisition module 110 detects an ECG signal of a testee. According to different requirements, the ECG signal to be acquired may be from 1-12 leads. 1 lead is primarily used to detect an HR and ECG abnormality related to the HR. Standard 3 leads or more may detect an ECG event related to myocardial ischemia excited by the exercise in real time, such as ST segment elevation or depression. A potential difference sensed by ECG electrodes which are pasted to various standard ECG positions on the chest is input into a differential amplification circuit in the module, is then converted into a digital signal through analog-to-digital conversion, and is transmitted to the electronic device 200' through a communication circuit (for example, Bluetooth). Now, these devices may be implemented by using standard highly-integrated chips. For example, the ECG electrodes may be implemented by using commercially available ECG pasters, and the ECG signal amplification and filtering module may be implemented by using an TLC2264 chip.

The human body exercise acquisition module 120 collects exercise data of the testee in real time, and uploads the data to the electronic device 200'. Specifically, exercise acceleration and an attitude angle of the testee in a walking process are measured. Common wearable exercise sensors comprise a micro-acceleration sensor, a gyroscope, a magnetic sensor or the like. The human body exercise acquisition module 120 is an integrated chip of a micro-digital acceleration sensor chip or digital acceleration sensor, a digital gyroscope, and a digital magnetic sensor, such as MPU-9150 from InvenSense (a registered trademark). There are two schemes of arranging an exercise sensor, and the simplest method is to arrange a single exercise sensor on a fixed part such as the chest or the torso to collect an attitude and an exercise signal of the torso. Many disturbances and errors may occur in the acceleration and gyroscope signals due to various factors during an exercise. In order to further improve the accuracy of gait analysis and step length measurement, the second scheme is to arrange an exercise senor unit on the torso and two legs respectively. In this case, the gait and the displacement can be relatively accurately calculated.

The treadmill exercise acquisition module 121 is primarily comprised of a speed sensor and a gradient sensor of the treadmill, and uploads measurement data to the electronic device 200'. A metabolic equivalent value may be calculated according to the speed and the gradient.

The electronic device 200' comprises the following modules: a test process control module 210, a treadmill mode control module 211, a voice and text prompt module 212, a man-machine interaction module 250, an ECG signal processing module 220, an exercise signal processing module 230, and a communication module 240. The handhold electronic device 200 acquires an identity (ID) and personal information of the testee from the workstation through the communication module 240, and transmits the ID and the personal information to the test program control module 210. The test program control module 210 generates a test program, and transmits the test program to the treadmill mode control module 211, the voice and text prompt module 212 and the man-machine interaction module 250 respectively. After the test is started, the handhold electronic device 200 receives the ECG signal and the exercise signal transmitted by the wearable component 100, which are then processed by the ECG signal processing module 220 and the exercise signal processing module 230 respectively, and a processing result is on the one hand transmitted to the test program control module 210 and is on the other hand uploaded to the workstation 300. Functions of various modules will be described below respectively.

The test program control module 210 is a central control module of the handhold electronic device. The test program control module 210 receives the ID and the personal information of the testee from the workstation 300, and generates an exercise test mode for this test. For example, the following mode may be selected for the Digital Cardiac Walking Test: the testee resting for 1 minute or more until the HR calms down; firstly starting walking at a normal speed, then accelerating gradually to a maximum speed as much as possible without any uncomfortable feeling and stopping walking until 6 minutes; and resting for 1 minute after stopping walking. In the whole test mode, the ECG data and the exercise data are recorded for 8 minutes, i.e., 1 minute for resting before walking, 6 minutes for walking, and 1 minute for resting after stopping walking. After the test mode is selected and the test is started, an instruction is transmitted to the voice and text prompt module 212 and the man-machine interaction module 250 so that the testee starts the test according to the instruction.

As another example, for the "Digital Cardiac Treadmill Test", the test program control module 210 selects a suitable exercise mode for example a common exercise load test such as Bruce, Naughton and ACIP schemes according to the personal information of the testee, and transmits an instruction to the treadmill mode control module 211, the voice and text prompt module 212 and the man-machine interaction interface module 250, so that the test is started according to the mode. Similarly, in order to acquire an RHR value and an HRE value, the whole test comprises resting for 1 minute before the exercise and resting for 1 minute after stopping the exercise.

The ECG signal processing module 220 receives the ECG signal from the ECG acquisition module 110 to implement three signal processing procedures, which are exercise disturbance removal, QRS structure detection and HR calculation, and ECG abnormality event detection. An algorithm for ECG signal processing may be known with reference to HuabinZheng, Jiankang Wu, A Real-Time QRS Detector Based on Discrete Wavelet Transform and Cubic Spline, Interpolational Journal of Telemedicine and e-Health, Vol. 14, ISS. 8, 2008, pp. 809-815.

An ECG processing result is transmitted to the test program control module 210, and the ECG signal and the HR are transmitted to the man-machine interaction module 250 for real-time display. If ECG abnormality occurs, the test program control module 210 issues an early warning through the voice and text prompt module 212 according to a pre-arranged plan. If the ECG abnormality is serious, the speed is reduced or even the exercise test is stopped through the treadmill mode control module 211 or the voice and text prompt module 212.

The exercise signal processing module 230 receives an exercise sensor signal from the human body exercise acquisition module 120 or the treadmill exercise acquisition module 121, and transmits a processing result to the communication module 240 and the test program control module 210.

Figure 6:
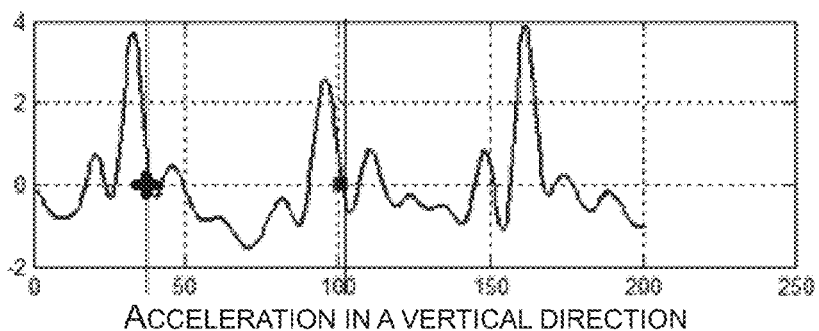
FIG. 6 illustrates data signal samples of an acceleration of an acceleration sensor on a chest according to an embodiment of the present disclosure.
Figure 6:
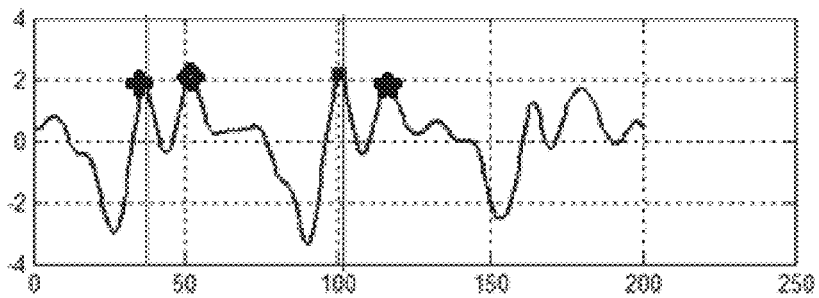

If the exercise sensor is implemented by using a single acceleration sensor, data signal samples of acceleration when the exercise sensor is placed on the chest are shown in FIG. 6. For each step, the acceleration in the vertical direction has two large waveform peaks. The first waveform peak represents "a moment when a heel touches the ground". In this case, the human body is under a large upward force, as indicated by crosses and blocks in the figure, and the acceleration in the forward direction is 0 at this time. The second waveform peak represents "a moment when a tiptoe leaves the ground" for the other foot. In this case, the weight is completely applied on the foot which touches the ground, which is in a thrust state against the ground. Therefore, a large upward force is generated, as indicated by diamonds and stars in the figure.

Therefore, basic gait parameters of a certain foot may be derived as follows:

(1)Proportion of double support phase=(horizontal coordinate corresponding to a diamond−horizontal coordinate corresponding to a cross)/period of a gait (2)Proportion of single support phase=(horizontal coordinate corresponding to a block−horizontal coordinate corresponding to a diamond)/period of a gait (3)Proportion of stand phase=(horizontal coordinate corresponding to a block−horizontal coordinate corresponding to a cross)/period of a gait (4)Proportion of swing phase=1−Proportion of stand phase A stride frequency may be accurately calculated according to the period of the acceleration signal.

A step length is a displacement within a gait period. In this case, a speed is calculated by implementing first-order integral on a forward acceleration component measured by an accelerator on the chest, and a displacement is calculated by implementing quadratic integral on the forward acceleration component. In order to remove an error due to a deviation when the wearable component is worn, when the wearable component is worn by a testee, the testee is required to stand for initialization and correction for 5 seconds.

If three exercise sensor units are used and arranged on a torso and legs respectively, a swing angle between the two legs may be accurately estimated, and accordingly, a step length may be calculated according to a length of the legs. A specific algorithm may be known with respect to XiaoliMeng, Zhiqiang Zhang, Jian-Kang Wu, Wai-Choong Wong, Hierarchical Information Fusion for Global Displacement Estimation in Microsensor Motion Capture, IEEE Trans. Biomed. Engineering, 60(7): 2052-2063, 2013.

The exercise intensity is represented by the Metabolic Equivalent (MET), and is defined as a ratio between a metabolic rate during an exercise and a metabolic rate during resting. The American College of Sports Medicine (ACSM) designs an MET equation for calculating a gross amount of oxygen consumption (Gross VO2) during walking, running, riding a stationary bicycle, and climbing steps (2006). An exercise speed is calculated according to gait time-space parameters, and thereby the MET is calculated.

Gross VO2=3.5+0.1×(speed)+1.8×(speed)×(percentage of gradient), wherein the percentage of gradient is 0% on a flat road.

Gross METs=Gross VO2÷3.5 ml/Kg/minute

Net METs=Gross METs−1MET (METs during resting)

The communication module 240 receives the ECG signal, the exercise signal and processing results thereof from the ECG signal processing module 220 and the exercise signal processing module 230, receives state information from the test program control module 210, and transmit them to the workstation 300. On the other hand, the communication module 240 receives information on the testee and a doctor's advice from the workstation 300, and transmits them to the test program control module 210.

The communication module 240 communicates with the workstation 300 in a wifi wireless communication manner during the Digital Cardiac Walking Test, and communicates with the workstation 300 in a wifi or wired network communication manner during the Digital Cardiac Treadmill Test.

The man-machine interaction module 250 is connected to the test program control module 210 to receive data or an instruction therefrom. The man-machine interaction module 250 provides a man-machine interaction interface. When the testee makes sure that he/she is ready to start, the testee clicks on a start pattern to start the test.

During the test, the man-machine interaction module 250 receives the ECG signal, the exercise signal and processing results thereof from the test program control module 210, displays the ECG signal, an HR, and marks representing abnormality in real time, and synchronously displays an exercise state, a stride frequency, a step length, and a distance.

The man-machine interaction module 250 alerts the testee of start or stop of the exercise or acceleration or deceleration of the exercise in a voice manner according to a process, and issues a warning of abnormality.

The man-machine interaction module 250 further provides an emergency button for use by the testee when feeling seriously uncomfortable.

The workstation 300 has three tasks. The first task is to receive and display signals and processing results from the electronic device 200'. The second task is to further analyze and process the data and processing results, to generate assessment parameters and reports of ECG, exercise, and HR exercise reaction of the testee. The third task is to provide interaction and information processing functions to medical workers.

The workstation 300 comprises a display, interaction and control module 310, an ECG and exercise signal analysis module 320, a report generation and data storage module 340, an emergency condition processing module 330 or the like.

The display, interaction and control module 310 receives and displays the ECG signal, the exercise signal and processing results thereof from the ECG and exercise signal analysis module 320, receives and displays a test report from the report generation and data storage module 340, receives and executes an instruction from medical workers, and provides data management, exercise test treadmill management, assessment and training management, real-time monitoring programs or the like to a testee/rehabilitation trainee.

The ECG and exercise signal analysis module 320 receives the ECG signal, the exercise signal and processing results thereof from the handhold electronic device, transmits them to the display, interaction and control module 310 for display, transmits them to the report generation and data storage module 340 to generate a report, and transmits abnormality to the emergency condition processing module 330. Further, the primary functions of the ECG and exercise signal analysis module 320 are to further analyze data, and deduce the following Chronotropic Competence indices.

The cardiopulmonary dynamic functions may be assessed by using an adaptive change in an HR in response to an exercise as a principal line. In recent years, researches have been developed widely and thoroughly on Chronotropic Incompetence internationally. A large number of clinical studies indicate that the Chronotropic Incompetence is an independent and specific index for cardiovascular events and a death rate. Experts believe that the Chronotropic Incompetence has not get enough attention as supposed clinically. This may be because the concepts of the definition and quantification of the Chronotropic Incompetence are relatively obscure and have no unified definition. In the embodiments of the present disclosure, the following Chronotropic Competence indices are defined and a corresponding measurement and calculation method is proposed:

RHR is defined as an HR when the body is in a resting state and a mood is in a calm-down state, which has a normal value range of 60-80 BPM.

CL is defined as Heart Rate Reserve (HRR), i.e., a maximum dynamic range which can be achieved by the heart to respond to the exercise. It not only depends on an activity capacity of the heart per se, but also depends on an autonomic nervous regulation capacity.

$$CL=HRR=(HR_{max}-HR_{rest})/(HR_{PredM}-HR_{rest})$$

wherein $HR_{max}$ and $HR_{rest}$ represent a maximum HR and a Resting Heart Rate (RHR) respectively, and $HR_{PredM}$ is a predicted value of the maximum HR, which is predicted by 220−age internationally, and recently is revised as 208−(0.7×Age) for healthy men, 206−(0.88×Age) for healthy women, and 164−(0.72×Age) for people with coronary disease. In the CPX, the testee is required to increase an amount of exercise to achieve conversion from an aerobic exercise state to an anaerobic exercise state, i.e., when an anaerobic threshold≥1.1, an exercise limit is achieved, and at this time, the HR is a maximum HR (HRmax), and thereby the CL value is calculated according to the above equation. In this case, a normal value of CL is in a range of 0.8-1.3.

As described above, in our country, due to consideration of risk as well as culture and recognition, there are very few patients who can achieve the anaerobic threshold in the CPX, and therefore the CL value in the original sense cannot be derived. In the walking test, due to the limit of such exercise form as walking, the HRmax achieved in the test is a maximum HR which can be achieved by the maximum walking effort. This is smaller than the CL when the limit exercise is achieved in CPX, and if CL>0.3, it is generally regarded to be normal. For example, for a 60 year old man, the maximum HR measured in the cardiopulmonary walking test is 110, and the RHR thereof is 76. Then, the CL can be derived according to the above equation as follows:

$$CL=(110-76)/(208-(0.7\times60)-76)=0.38$$

The value of CL in the cardiopulmonary walking test is widely applied to predict cardiovascular events, death incidents, or a threshold for disease prognosis. There have been a large number of clinic researches internationally.

The CR is a change rate of an HR to exercise equivalents, or a change of an HR per unit exercise equivalent, which is a reaction speed of the heart to the exercise:

$$CR=(HR_{stage}-HR_{rest})/(MET_{stage}-1)$$

Wherein $HR_{stage}$ and $MET_{stage}$ represent an HR and an exercise metabolic equivalent at a certain time during the test respectively, and $HR_{rest}$ represents an RHR of the testee. For a healthy person, such change rate in the above equation is closely linear, and an increase value of the HR per MET is about 10 BPM.

The HRE has been proven to be a very useful prognosis index. In the 6 minutes walking test, it is more important than a walking distance. The HRE is defined as a difference between the maximum HR in an exercise and an HR 1 minute after the exercise is stopped. It is a danger index for cardiovascular disease, and is closely related to the death rate. HRE≤12 is a reference value for defining abnormality. Kopecky etc. has developed a tracking study on the HR exercise test for 6546 persons with an average age of 49 and without a history of cardiovascular disease for 10 years. In 285 dead persons of the 6546 persons, a value of the HRE less than 12 is an independent all-cause mortality index.

Thus, the CCIs are defined, which comprise four indices, which are RHR, CL, CR and HRE.

When the above indices are measured and calculated, measured key parameters should be attached, comprising $HR_{PredM}$, $HR_{Max}$, $MET_{Peak}$, $HR_{Stage}$ and $MET_{Stage}$ in the walking test. For the same patient, a change in the exercise intensity which is represented by the METs when the maximum HR is achieved also represents a change in the exercise capability thereof.

The report generation and data storage module 340 receives the signals and processing results from the ECG and exercise signal analysis module 320, and generates a report.

During each cardiac exercise test, no matter whether a walking test or a treadmill exercise test, the device records ECG data in a resting state 1 minute before the exercise test, ECG and exercise data during several minutes after the exercise is started, and ECG data 1 minute after the exercise test is stopped in real time. During the exercise test, on the premise of security, the testee is encouraged to accelerate the exercise as much as possible. The $HR_{rest}$, the $HR_{stage}$ at any time, and the $HR_{max}$ during an exercise are acquired according to the actually measured ECG data.

The above exercise-HR parameters are summed up to form the following content in the test report:

| CCIs | Reference value |
|---|---|
| RHR | 60-80 pbm |
| Max HR in Exercise | 220-age |
| MET at Max HR | |
| Walking Distance Grading | I ≤ 300 < II ≤ 375 < III ≤ 450 < IV |
| CT | ≥0.8 (when the CPX achieves an anaerobic threshold) |
| CR | ~10 BPM |
| HRE value | ≥12 BPM | and typical gait parameters in the following table.

| Parts | Singlesupport phase | Swing phase | Stand phase | Step length |
|---|---|---|---|---|
| Left | 39.96% | 39.29% | 60.71% | 41.6 cm |
| Right | 39.29% | 39.96% | 60.04% | 45.6 cm |

The report generation and data storage module 340 stores the data of the testee into a database according to an instruction from a user, and uploads the data to the hospital information system.

The emergency condition processing module 330 receives an abnormal signal from the ECG and exercise signal analysis module 320, proposes an emergency processing scheme, and transmits a processing instruction to the handhold electronic device 200 or the electronic device 200' after receiving confirmation from the medical workers.

Up to this point, a device and system for digital cardiac exercise testing are described. However, those skilled in the art can anticipate that the above device and system according to the present disclosure can be further generalized into an integrated system for assessment, rehabilitation and monitoring. It will be described by taking the Digital Cardiac Treadmill Test as an example. The process is similar for the Digital walking exercise Test. A doctor workstation is equipped with a database of all testees/rehabilitation trainees, and provides data management, ECG exercise test treadmill management, assessment and training management, real-time monitoring programs or the like. In a case that a workstation is connected to multiple treadmills, the flowchart of testing cardiac exercise functions according to the embodiments of the present disclosure will be described in detail below.

Figure 7:
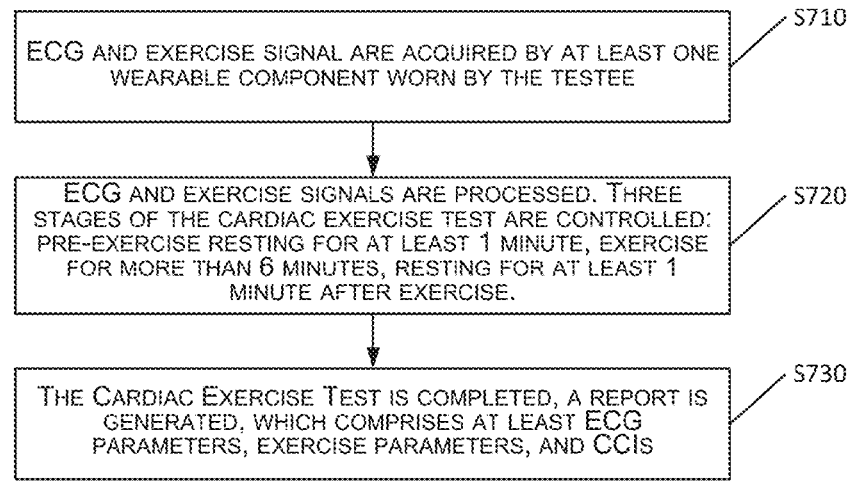
FIG. 7 is a flowchart illustrating a method for testing cardiac exercise functions according to an embodiment of the present disclosure.

FIG. 7 is a flowchart of a method for testing cardiac exercise functions according to an embodiment of the present disclosure. As shown in FIG. 7, in step S710, an ECG signal of a testee and an exercise signal of the testee without or with a load are acquired by at least one wearable component worn by the testee.

For example, a testee and a corresponding treadmill as well as exercise testing assessment are selected by a doctor using the display, interaction and control module 310, and an instruction and data of the testee are transmitted by the workstation to the handhold electronic device, i.e., the treadmill console. Then, the wearable component 100 is worn by the testee, and is ready to start. The electronic device 200' receives the instruction through the communication module 240, and the test program control module 210 selects an exercise mode and duration according to the data of the testee, transmits them to the workstation, and after receiving confirmation from medical workers, starts an assessment program to start assessment.

Next, in step S720, the ECG signal and the exercise signal are processed, and a process of cardiac exercise testing is controlled. The process of cardiac exercise testing comprises the following three periods of resting for at least 1 minute before an exercise test, exercising for 6 minutes or more in a certain mode after the exercise test is started, and resting for 1 minute or more after the exercise is stopped.

For example, the information of the testee, the exercise mode, the ECG signal or the like are displayed in real time on a display of the man-machine interaction module 250. The test program control module 210 uploads the exercise mode, the current exercise parameters and the ECG data in real time to the workstation 300 through the communication module 240. The man-machine interaction module 250 has an emergency button thereon for use by the testee when feeling uncomfortable.

In step S730, the process of cardiac exercise testing is completed under the monitoring of a user, and a test report is generated, wherein the report comprises at least ECG parameters, exercise parameters and CCIs.

For example, a doctor monitors the testee in real time through the display, interaction and control module 310 of the workstation, and takes action and issues an order anytime through the emergency condition processing module 330 according to the real-time information. Thus, after the exercise test is completed according to the testing scheme, the test program control module 210 transmits a notification to the testee through the man-machine interaction module 250 and transmits a notification to the medical workers through the display, interaction and control module 310. The display, interaction and control module 310 notifies the report generation and data storage module 340 to generate a test report, stores the test report into the database after receiving confirmation from the medial workers, and uploads it to the hospital information system.

According to some embodiments, the report comprises ECG interpretation parameters, particularly an ST shape shift, exercise parameters, and chronotropic competence indices (Resting heart rate, chronotropic limit, chronotropic rate, HR recovery or the like).

Figure 8:
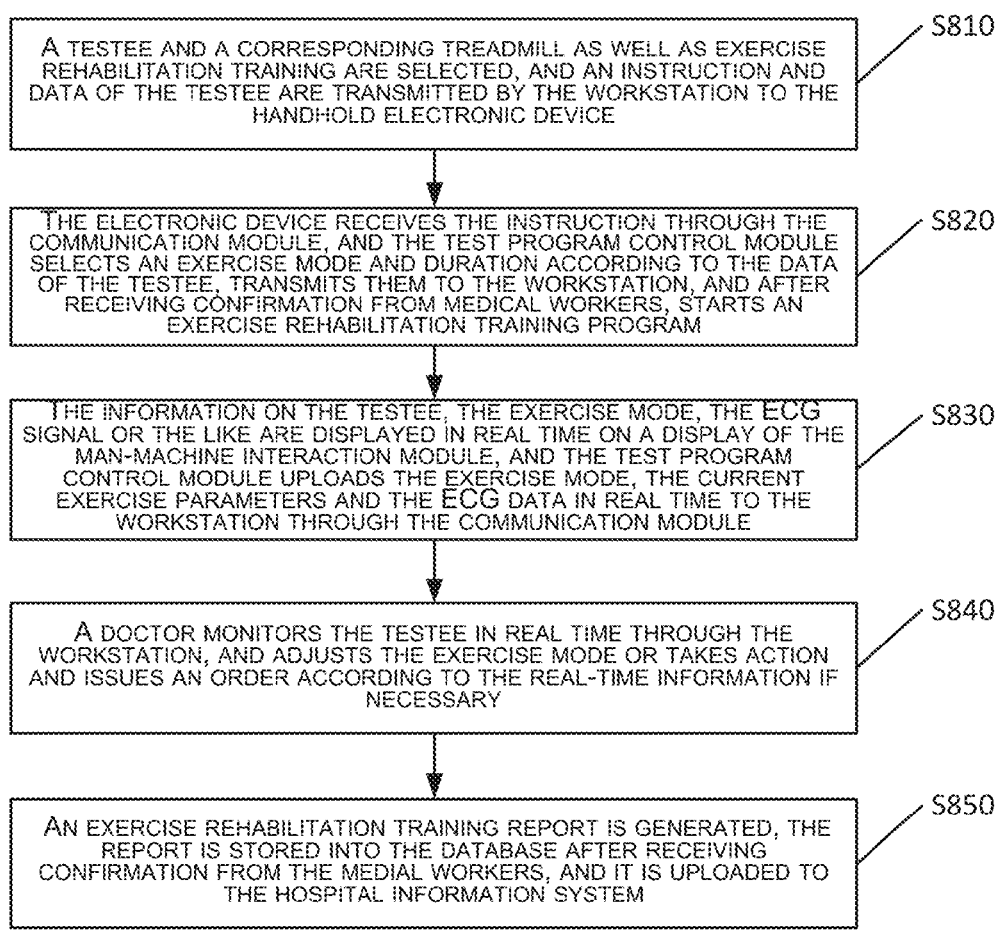
FIG. 8 is a diagram of applying a testing method according to an embodiment of the present disclosure to a training, monitoring and assessing process.

FIG. 8 is a diagram of applying a testing method according to an embodiment of the present disclosure to a training, monitoring and assessing process.

For example, in a case that a workstation is connected to multiple treadmills, the testing method according to the embodiment of the present disclosure may be applied to a training, monitoring and assessing process of a cardiac exercise of a testee, which will be described in detail below.

In step S810, a testee and a corresponding treadmill as well as exercise rehabilitation training are selected by a doctor using the display, interaction and control module 310, and an instruction and data of the testee are transmitted by the workstation to the handhold electronic device, i.e., the treadmill console.

In step S820, the wearable component 100 is worn by the testee, and is ready to start. The electronic device 200' receives the instruction through the communication module 240, and the test program control module 210 selects an exercise mode and duration according to the data of the testee, transmits them to the workstation, and after receiving confirmation from medical workers, starts an exercise rehabilitation training program to start training.

In step S830, the information on the testee, the exercise mode, the ECG signal or the like are displayed in real time on a display of the man-machine interaction module 250. The test program control module 210 uploads the exercise mode, the current exercise parameters and the ECG data in real time to the workstation 300 through the communication module 240. The man-machine interaction module 250 has an emergency button thereon for use by the testee when feeling uncomfortable.

In step S840, a doctor monitors the testee in real time through the display, interaction and control module 310 of the workstation, and adjusts the exercise mode or takes action and issues an order any time according to the real-time information through the emergency condition processing module 330 if necessary.

In step S850, after the exercise rehabilitation training is completed according to the training scheme, the test program control module 210 transmits a notification to the testee through the man-machine interaction module 250 and transmits a notification to the medical workers through the display, interaction and control module 310. The display, interaction and control module 310 notifies the report generation and data storage module 340 to generate an exercise rehabilitation training report, stores the report into the database after receiving confirmation from the medial workers, and uploads it to the hospital information system. For example, the exercise rehabilitation training report comprises ECG interpretation parameters, particularly an ST shape; exercise parameters, and chronotropic competence indices (Resting Heart Rate (RHR), Chronotropic Limit (CL), Chronotropic Rate (CR), and Heartrate Recovery after Exercise (HRE).

The device and system for cardiac exercise testing according to the above embodiments provide a series of ECG, exercise and chronotropic competence digital metrics, which comprehensively reflect the cardiovascular dynamic functions, and provide a basis for diagnosis, prevention and rehabilitation of cardiovascular disease. The digital metrics thereof are easier to apply than the CPX. For example, the "Digital Cardiac Walking Test" uses a wearable device without requirements for a particular place, which is easy to learn and use, and is suitable for various hospitals. The "Digital Cardiac Treadmill Test" is convenient to manage, and is more suitable for hospitals and rehabilitation centers.

Further, the "device and system for digital cardiac exercise testing" is simple and convenient, and can be used anytime anywhere, which largely simplifies complexity of the cardiopulmonary function exercise test, and can play a larger and more comprehensive function in the diagnosis, prevention and rehabilitation of a person with cardiovascular disease. The "device and system for digital cardiac exercise testing" is a digital device, and can report data to a doctor through a network any time anywhere.

The foregoing detailed description has set forth various embodiments of the device and system for testing a cardiac exercise via the use of diagrams, flowcharts, and/or examples. In a case that such diagrams, flowcharts, and/or examples contain one or more functions and/or operations, it will be understood by those skilled in the art that each function and/or operation within such diagrams, flowcharts or examples may be implemented, individually and/or collectively, by a wide range of structures, hardware, software, firmware, or virtually any combination thereof. In one embodiment, several portions of the subject matter described in the embodiments of the present disclosure may be implemented via Application Specific Integrated Circuits (ASICs), Field Programmable Gate Arrays (FPGAs), Digital Signal Processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of those skilled in the art in ray of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present disclosure has been described with reference to several typical embodiments, it is apparent to those skilled in the art that the terms are used for illustration and explanation purpose and not for limitation. The present disclosure may be practiced in various forms without departing from the spirit or essence of the present disclosure. It should be understood that the embodiments are not limited to any of the foregoing details, and shall be interpreted broadly within the spirit and scope as defined by the following claims. Therefore, all of modifications and alternatives falling within the scope of the claims or equivalents thereof are to be encompassed by the claims as attached.

I claim:

1. A system for testing cardiac exercise functions, comprising:
    at least one wearable component worn by a testee, comprising an ECG acquisition module configured to acquire ECG signal of the testee, and an exercise acquisition module configured to acquire an exercise signal of the testee without or with a load;
    a handhold electronic device configured to acquire the ECG signal and the exercise signal of the testee from the at least one wearable component in a wired or wireless communication manner, process the ECG signal and the exercise signal, and control a process of cardiac exercise testing; and
    a workstation connected to the handhold electronic device in a wireless or wired communication manner, configured to receive data from the handhold electronic device, complete the process of cardiac exercise testing under the monitoring of a user, and generate a test report comprising at least ECG parameters, exercise parameters and Chronotropic Competence Indices (CCIs).

2. The system according to claim 1, wherein the handhold electronic device is configured to process the ECG signal and the exercise signal in real time in the following three periods of resting for at least 1 minute before an exercise test, exercising for 6 minutes or more in a certain mode after the exercise test is started, and resting for 1 minute or more after the exercise is stopped.

3. The system according to claim 1, wherein the CCIs comprise Resting Heart Rate (RHR),Chronotropic Limit (CL), Chronotropic Rate (CR), and Heartrate Recovery after Exercise (HRE).

4. The system according to claim 3, wherein the CR is measured according to the following equation:

$$CR=(HR_{stage}-HR_{rest})/(MET_{stage}-1)$$

wherein $HR_{stage}$ and $MET_{stage}$ represent a heart rate and an exercise metabolic equivalent of the testee at a certain time during the test respectively, and $HR_{rest}$ represents a heart rate of the testee during resting.

5. The system according to claim 3, wherein the chronotropic limits measured according to the following equation:

$$CL=(HR_{max}-HR_{rest})/(HR_{PredM}-HR_{rest})$$

wherein $HR_{max}$ and $HR_{rest}$ represent the maximum heart rate and Resting Heart Rate (RHR) respectively, and $HR_{PredM}$ represents a predicted value of the maximum heart rate.

6. The system according to claim 3, wherein the HRE is defined as the difference between the maximum exercise heart rate and the heart rate 1 minute after the exercise is stopped, which represents a speed at which the heart rate recovers to the RHR after the exercise is stopped.

7. The system according to claim 1, wherein the handhold electronic device comprises a man-machine interaction module configured to alert the testee of start or stop of the exercise or acceleration or deceleration of the exercise in a voice or image manner, and display information, an exercise mode, and an ECG signal of the testee in real time, and configured with an emergency button for use by the testee when feeling uncomfortable.

8. The system according to claim 1, wherein the ECG acquisition module is worn on the chest of the testee, and comprises at least one lead, and the exercise acquisition module is configured to measure exercise acceleration and an attitude angle of the testee during the exercise.

9. The system according to claim 8, wherein the exercise acquisition module comprises an exercise sensing unit arranged on a torso of the testee and exercise sensing units arranged on two legs of the testee.

10. A system for testing cardiac exercise functions, comprising:
    at least one wearable component worn by a testee, comprising an ECG acquisition module configured to acquire an ECG signal of the testee;
    a treadmill comprising an exercise acquisition module configured to acquire an exercise signal of the testee without or with a load, and an electronic device configured to acquire the ECG signal of the testee from the at least one wearable component and the exercise signal of the testee from the exercise acquisition module in a wired or wireless communication manner, process the ECG signal and the exercise signal, and control a process of cardiac exercise testing; and
    a workstation connected to the electronic device in in a wireless or wired communication manner, configured to receive data from the electronic device, complete the process of cardiac exercise testing under the monitoring of a user, and generate a test report comprising at least ECG parameters, exercise parameters and Chronotropic Competence Indices (CCIs).

11. The system according to claim 10, wherein the electronic device is configured to process the ECG signal and the exercise signal in real time in the following three periods of resting for at least 1 minute before an exercise test, exercising for 6 minutes or more in a certain mode after the exercise test is started, and resting for 1 minute or more after the exercise is stopped.

12. The system according to claim 10, wherein the exercise acquisition module comprises a speed sensor and a gradient sensor arranged on the treadmill.

13. The system according to claim 12, wherein the CCIs comprise Resting Heart Rate (RHM), Chronotropic Limit (CL), Chronotropic Rate (CR), and Heartrate Recovery after Exercise (HRE).

14. The system according to claim 13, wherein the CR is measured according to the following equation:

$$CR=(HR_{stage}-HR_{rest})/(MET_{stage}-1)$$

wherein $HR_{stage}$ and $MET_{stage}$ represent a heart rate and an exercise metabolic equivalent of the testee at a certain time during the test respectively, and $HR_{rest}$ represents a heart rate of the testee during resting.

15. The system according to claim 13, wherein the chronotropic limits measured according to the following equation:

$$CL=(HR_{max}-HR_{rest})/(HR_{PredM}-HR_{rest})$$

wherein $HR_{max}$ and $HR_{rest}$ represent a maximum heart rate and a Resting Heart Rate (RHR) respectively, and $HR_{PredM}$ represents a predicted value of the maximum heart rate.

16. The system according to claim 13, wherein the HRE is defined as the difference between the maximum exercise heart rate and the heart rate 1 minute after the exercise is stopped, which represents a speed at which the heart rate recovers to the RHR after the exercise is stopped.

17. A device for testing cardiac exercise functions, comprising:
    an exercise acquisition module configured to acquire an exercise signal of a testee without or with a load, wherein at least one wearable component is worn by the testee, and comprises an ECG acquisition module configured to acquire an ECG signal of the testee; and
    an electronic device configured to acquire the ECG signal of the testee from the at least one wearable component and the exercise signal of the testee from the exercise acquisition module in a wired or wireless communication manner, process the ECG signal and the exercise signal, and control a process of cardiac exercise testing,
    wherein the process of cardiac exercise testing is completed according to the data of the electronic device under the monitoring of a user, and a test report is generated, wherein the test report comprises at least ECG parameters, exercise parameters and Chronotropic Competence Indices (CCIs).

18. An electronic device, comprising:
    a communication module configured to acquire an ECG signal of a testee and an exercise signal of the testee without or with a load from at least one wearable component worn by the testee in a wired or wireless communication manner;
    a signal processing module configured to process the ECG signal and the exercise signal obtained by the communication module in the following three periods of resting for at least 1 minute before an exercise test, exercising for 6 minutes or more in a certain mode after the exercise test is started, and resting for 1 minute or more after the exercise is stopped; and a control module configured to control a process of cardiac exercise testing.

19. A method for testing cardiac exercise functions, comprising:

perceiving, by at least one wearable component worn by a testee, an ECG signal of the testee and an exercise signal of the testee without or with a load;

processing the ECG signal and the exercise signal, and controlling a process of cardiac exercise testing, wherein the process of cardiac exercise testing comprises the following three periods of resting for at least 1 minute before an exercise test, exercising for 6 minutes or more in a certain mode after the exercise test is started, and resting for 1 minute or more after the exercise is stopped; and completing the process of cardiac exercise testing under the monitoring of a user, and generating a test report comprising at least ECG parameters, exercise parameters and Chronotropic Competence Indices (CCIs).

* * * * *